US00PP30154P2

(12) United States Plant Patent
Heimovaara

(10) Patent No.: US PP30,154 P2
(45) Date of Patent: Jan. 29, 2019

(54) ***CHRYSANTHEMUM* PLANT NAMED 'ZANMULPINE'**

(50) Latin Name: ***Chrysanthemum* x *morifolium* Ramat.**
Varietal Denomination: Zanmulpine

(71) Applicant: Van Zanten Breeding BV, Aalsmeer (NL)

(72) Inventor: Sjoukje Heimovaara, Valkenburg (NL)

(73) Assignee: Van Zanten Breeding BV, Aalsmeer (NL)

( * ) Notice: Subject to any disclaimer, the term of this patent is extended or adjusted under 35 U.S.C. 154(b) by 0 days.

(21) Appl. No.: 15/732,815

(22) Filed: Jan. 4, 2018

(51) Int. Cl.
*A01H 5/02* (2018.01)

(52) U.S. Cl.
USPC ..... Plt./294

(58) Field of Classification Search
USPC ..... Plt./294
See application file for complete search history.

*Primary Examiner* — Annette H Para
(74) *Attorney, Agent, or Firm* — Steptoe & Johnson LLP

(57) ABSTRACT

A *chrysanthemum* plant named 'Zanmulpine' characterized by its medium sized blooms with white ray florets and prolific branching; natural season flowering date October 9; blooming for a period of 5 weeks.

3 Drawing Sheets

Botanical designation: *Chrysanthemum* x *morifolium* Ramat.

Cultivar denomination: 'Zanmulpine'.

RELATED CULTIVARS

This new plant cultivar 'Zanmulpine' is of the botanical classification *Chrysanthemum* x *morifolium* Ramat.

BACKGROUND OF THE INVENTION

The present invention relates to a new and distinct cultivar of *chrysanthemum* plant, botanically known as *Chrysanthemum* x *morifolium* Ramat., commercially known as a garden mum, and hereinafter referred to by the cultivar denomination 'Zanmulpine'. 'Zanmulpine' is a product of a breeding and selection program for outdoor pot mums (garden mums) which had the objective of creating new cultivars with a double type inflorescence, a natural season flowering date around October 9, blooming for a period of 5 weeks. 'Zanmulpine' is a seedling resulting from a cross of the female parent 36979 (unpatented) with the male parent 37034 (unpatented). Plants of the new cultivar 'Zanmulpine' differ from plants of the female parent in the ray-floret color, ray-florets of the seedling are white, while those of female parent show some pink coloration due to anthocyanin formation at low temperatures. Plants of the new cultivar 'Zanmulpine' differ from plants of the male parent in the following characteristics. (1) Inflorescence color. And (2) Inflorescence size. (1) Inflorescences of the seedling are more white than those of the male parent.(2) Inflorescences of the seedling are larger than those of the male parents.

The new and distinct cultivar was discovered and selected as a flowering plant by Sjoukje Heimovaara on a cultivated field in Rijsenhout, The Netherlands in October 2012. The first act of asexual production of 'Zanmulpine' was accomplished when vegetative cuttings from the initial selection were propagated further in a controlled environment in Rijsenhout, the Netherlands, in December 2012. In summer, about 6-8 days are needed to initiate roots in cuttings of the new cultivar, after another 5 days rooted plants are formed.

The new cultivar has been found to retain its distinctive characteristics through successive propagations.

BRIEF DESCRIPTION OF THE DRAWINGS

The present invention of a new and distinct variety of *chrysanthemum* (of about 20 weeks) is shown in the accompanying drawings, the color being as nearly true as possible with color photographs of this type.

DESCRIPTION OF THE INVENTION

Figure 1:
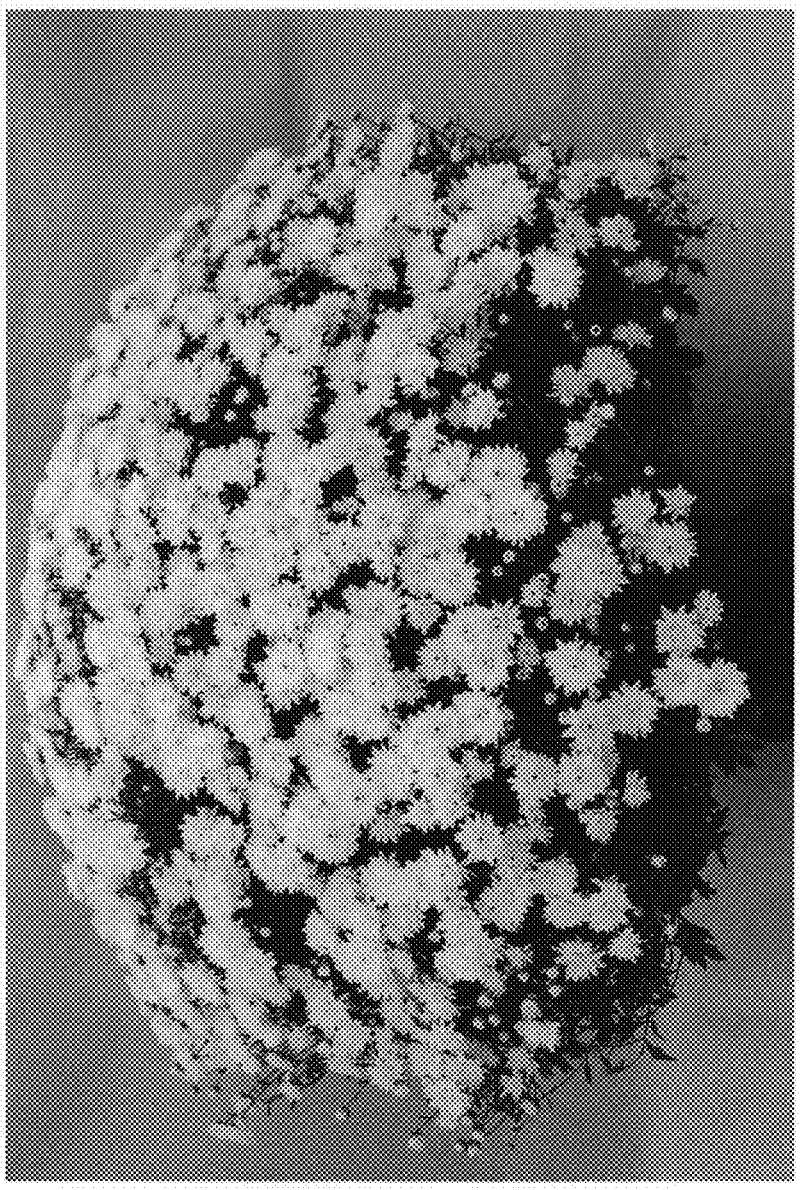
FIG. 1 shows a plant of the cultivar in full bloom.
Figure 2:
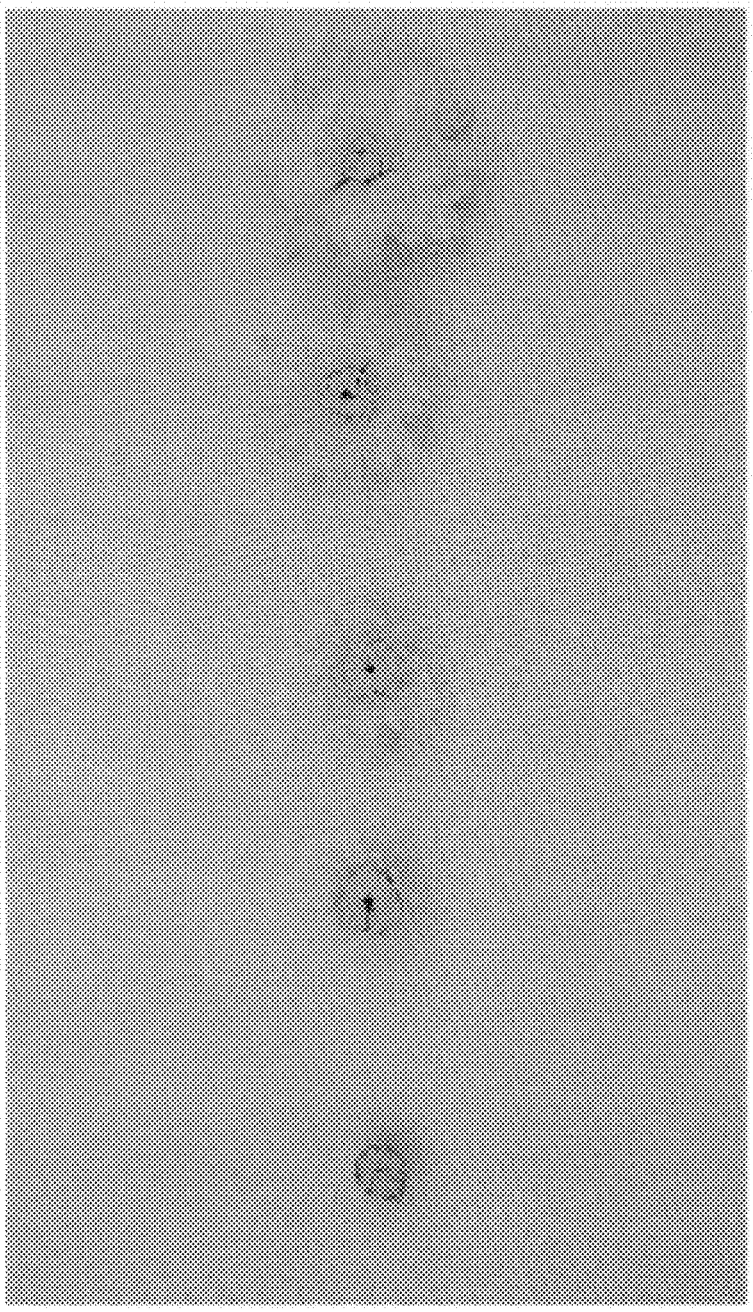
FIG. 2 shows the various stages of bloom of the new cultivar.
Figure 3:
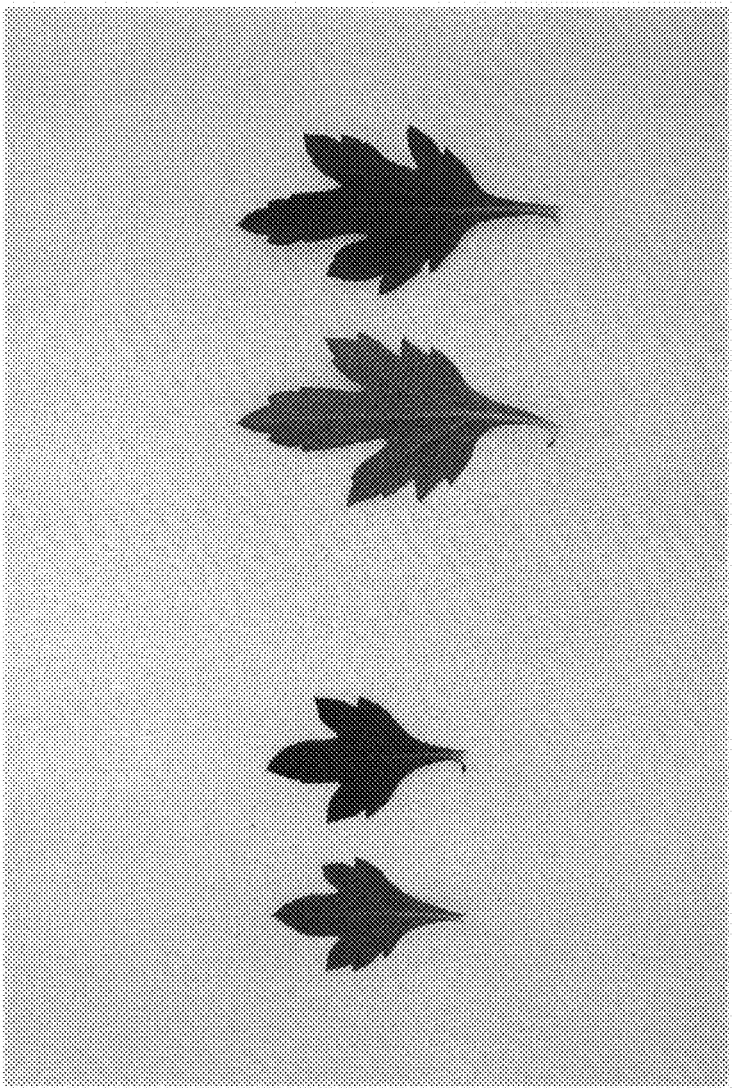
FIG. 3 shows the various stages of foliage of the new cultivar.

The observations and measurements were gathered from plants in the period of 18 to 23 weeks of age grown outdoor in Rijsenhout, the Netherlands, under natural day length and temperature and planted in week 23 in 2017, receiving drip irrigation. The natural blooming date of this crop was October 9 (week 41). The average height of the plants was 40 cm. No growth retardants were used. No tests were done on disease or insect resistance or susceptibility. No tests were done on cold or drought tolerance. This new variety produces medium sized blooms with white ray florets blooming for a period of 5 weeks.

From the cultivars known to the inventor the most similar existing cultivar in comparison to 'Zanmulpine' is 'Zanmudove' (U.S. Plant Pat. No. 24,618). When 'Zanmudove' and 'Zanmulpine' are being compared the following differences are noticed: (1). Natural season blooming date. And (2). Plant vigor. (1). Plants of 'Zanmulpine' flower later in the season than plant of 'Zanmudove'. (2). Flowering plants of 'Zanmulpine' are larger than those of 'Zanmudove'

The following is a description of the plant and characteristics that distinguish 'Zanmulpine' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, sixth edition (2015).

TABLE 1

Botanical Description of Chrysanthemum × morifolium Ramat. 'Zanmulpine'

| | |
|---|---|
| **Bud** | |
| Size: | Small; cross-section 6 mm, height 5 mm |
| Shape: | Round |
| Texture: | Pubescent |
| Outside color: | Greyed-green 191B |
| **Phyllaries** | |
| Number: | 21-22, arranged in 3 rows |
| Shape: | Elliptic |
| Apex: | Acute |
| Base: | Truncate |
| Margin: | Entire |
| Color: | Upper side: Green 143c |
| Lower side: | Greyed-green 191C |
| Length and width: | 3 mm; 1.5 mm |
| Texture: | Pubescent |
| **Inflorescences** | |
| Type: | Double |
| Height: | 1-3 cm |
| Diameter: | 4 cm |
| Peduncle length: | 7.5 cm |
| Peduncle color: | Greyed-green 190A |
| Peduncle diameter: | 1.5 mm |
| Peduncle texture: | Pubescent |
| Number per branch: | About 5-6 inflorescences |
| Duration of flowering: | 5 weeks |
| Seeds: | Produced in small quantities, ovate, Greyed-browsn 199A, length 1.5 mm, diameter 0.5 mm; texture: rough with ribs |
| Fragrance: | Faint chrysanthemum odor |
| **Color inflorescences** | |
| Center of inflorescence: | Immature stage: White 155A; Mature stage: White 155A |
| Color of upper side of ray florets: | White NN155D |
| Color of lower side of ray florets: | White NN155D |
| Tonality from distance: | A garden mum with white blooms and a cream center |
| Color of ray florets after : aging of the plant | White NN155D |
| **Ray florets** | |
| Number of types: | One |
| Type: | Ligulate |
| Rows: | About 15 |
| Texture: | Upper and lower side smooth |
| Number: | 180-200 |
| Shape: | Elliptic |
| Apex: | Pointed |
| Base: | Acute |
| Cross-section: | Flat |
| Longitudinal axis: | Straight |
| Length of corolla tube: | 1-3 mm |
| Diameter corolla tube: | 1 mm |
| Ray floret margin: | Entire |
| Ray floret length: | 1-2.3 cm |
| Ray-floret width: | 2-5 mm |
| Ratio length/width: | Medium |
| Disc florets | Absent |
| **Receptacle** | |
| Color: | Yellow-green 145D |
| Shape: | Domed raised |
| Height: | 4 mm |
| Diameter: | 3 mm |

TABLE 1-continued

Botanical Description of Chrysanthemum × morifolium Ramat. 'Zanmulpine'

| | |
|---|---|
| **Reproductive Organs** | |
| Androecium: | Absent |
| Pollen: | Lacking |
| Gynoecium: | Present in ray florets |
| Style color: | Yellow-green 154C |
| Style length: | 4 mm |
| Stigma color: | Yellow 7A |
| Stigma width: | 1 mm |
| Ovary: | Enclosed in calyx |
| Ovary color: | Yellow-green 149D |
| **Plant** | |
| Type: | Bushy |
| Growth habit: | Spherical shape |
| Growth rate: | Vigorous |
| Height: | 35-45 cm |
| Width: | 60-70 cm |
| Stem color: | Greyed-brown 199A |
| Stem strength: | Not strong |
| Stem brittleness: | Brittle |
| Stem anthocyanin coloration: | Absent |
| Internode length: | 1-1.5 cm |
| Length of lateral branch: | From top to bottom 23 cm |
| Lateral branch color: | Yellow-Green 147 C |
| Lateral branch, attachment: | Weak |
| Lateral branch diameter: | 2.5 mm |
| Lateral branch, texture: | Pubescent with ribs |
| Branching (average number of lateral branches): | Medium with 8-9 breaks after pinching Natural season blooming date: October 9 (week 41) in Rijsenhout, the Netherlands |
| Roots - habits: | Fine, freely branching |
| Roots - color: | White 155A |
| **Foliage** | |
| Glossiness: | Leaf upper side: very weak<br>Leaf lower side: absent |
| Leaf color: | Upper side: Green NN137A<br>Lower side: Green 138A |
| Color midvein: | Upper side: Yellow-green 147D<br>Lower side: Yellow-green 148D |
| Size: | Small; length 3-4.5 cm, width 2.3-2.6 cm |
| Quantity (number per lateral branches): | 23-25 |
| Shape: | Elliptic |
| Texture upper side: | Sparsely pubescent |
| Texture under side: | Pubescent |
| Venation arrangement: | Pinnate |
| Shape of margin: | Serrated |
| Shape of base of sinus between lateral lobes: | Rounded |
| Margin of sinus between lateral lobes: | Diverging |
| Shape of base: | Attenuate to truncate |
| Apex: | Mucronulate |
| Petiole strength: | Weak |
| Petiole attitude: | Moderately upwards |
| Petiole length: | 0.8 cm |
| Petiole diameter: | 1-2 mm |
| Petiole color: | Yellow-green 147D |
| Stipules: | Very small |

TABLE 2

Differences with the comparison variety, when grown under identical conditions

| | 'Zanmulpine' | 'Zanmudove' |
|---|---|---|
| Natural season blooming date | Week 41 | Week 39 |
| Plant size | 40 cm | 30 cm |

I claim:

1. A new and distinct *chrysanthemum* plant named 'Zanmulpine' as described and illustrated.

* * * * *